United States Patent [19]
Wall et al.

[11] Patent Number: 5,364,858
[45] Date of Patent: *Nov. 15, 1994

[54] CAMPTOTHECIN ANALOGS AS POTENT INHIBITORS OF TOPOISOMERASE I

[75] Inventors: Monroe E. Wall, Chapel Hill; Mansukh C. Wani, Durham; Allan W. Nicholas; Govindarajan Manikumar, both of Raleigh, all of N.C.

[73] Assignee: Research Triangle Institute, Research Triangle Park, N.C.

[*] Notice: The portion of the term of this patent subsequent to Sep. 14, 2010 has been disclaimed.

[21] Appl. No.: 986,696

[22] Filed: Dec. 8, 1992

Related U.S. Application Data

[60] Division of Ser. No. 600,825, Oct. 22, 1990, Pat. No. 5,244,903, and a continuation-in-part of Ser. No. 511,953, Apr. 17, 1990, Pat. No. 5,053,512, said Ser. No. 600,825, is a continuation-in-part of Ser. No. 424,910, Oct. 23, 1989, Pat. No. 5,106,742, which is a continuation-in-part of Ser. No. 32,449, Mar. 31, 1987, Pat. No. 4,894,456, said Ser. No. 511,953, is a continuation of Ser. No. 38,157, Apr. 14, 1987, abandoned.

[51] Int. Cl.$^5$ .................................. A61K 31/44
[52] U.S. Cl. .................................. 514/279; 514/283
[58] Field of Search .................................. 514/279, 283

[56] References Cited

U.S. PATENT DOCUMENTS

| | | |
|---|---|---|
| 4,031,098 | 6/1977 | Sugasawa . |
| 4,473,692 | 9/1984 | Miyasaka et al. . |
| 4,545,880 | 10/1985 | Miyasaka et al. . |
| 4,604,463 | 8/1986 | Miyasaka et al. . |
| 4,894,456 | 1/1990 | Wall et al. . |
| 4,914,205 | 4/1990 | Sawada et al. . |

FOREIGN PATENT DOCUMENTS

| | | |
|---|---|---|
| 0074256 | 3/1983 | European Pat. Off. . |
| 0220601 | 2/1986 | European Pat. Off. . |
| 321122 | 12/1987 | European Pat. Off. . |
| 5905188 | 6/1982 | Japan . |
| 57-116015 | 7/1982 | Japan . |
| 5951289 | 9/1982 | Japan . |
| 59-46284 | 3/1984 | Japan . |
| 59-51287 | 3/1984 | Japan . |
| 6185389 | 10/1984 | Japan . |
| 61-50985 | 3/1986 | Japan . |
| 61-85319 | 4/1986 | Japan . |

OTHER PUBLICATIONS

*Cancer Research*, (1989), vol. 49, 4385–5489, "DNA Topoisomerase I-Meditated DNA Cleavage and Cytotixicity of Camptothecin Analogues", Hisang et al.

*Cancer Research*, (1989), vol. 49, 1465–1469, "Structure-Activity Study Of The Actions Of Camptothecin Derivatives On Mammalian Topoisomerase I . . . " Jaxel et al.

*The Journal Of Biological Chemistry*, (1985, 260, 14873–14878, "Camptothecin Induces Protein-Linked DNA Breaks Via Mammalian DNA Topoisomerase I" Hsiang et al.

*J. Med. Chem*, (1980), 23, 544–560, "Plant Antitumor Agents. 18.[1] Synthesis And Bilogical Activity Of Camptothecin Analogues", Wani et al.

*J. Med. Chem*, (1986), 29, 1553–1555, "Plant Antitumor Agents 22.[1] Isolation Of 11-Hydroxycamptothecin From *Camptotheca acuminata* Decne . . . " Wall et al.

*Journal Of Labelled Compounds And Radiopharmaceuticals*, (1981), 18, 319–329, "The Preparation of Tritium And Deuterium-Labelled Camptothecin", Ronman et al.

*J. Medicinal Chemistry*, (1987), 30, 1774–1779, "Plant Antitumor Agents 25.[1] Total Synthesis And Antileukemic Activity Of Ring A . . . ". Wani et al.

(List continued on next page.)

*Primary Examiner*—Jerome D. Goldberg
*Attorney, Agent, or Firm*—Oblon, Spivak, McClelland, Maier & Neustadt

[57] ABSTRACT

A method for synthesizing camptothecin and camptothecin analogs using a novel hydroxyl-containing tricyclic intermediate and the camptothecin analogs produced by the process. The camptothecin analogs are effective inhibitors of topoisomerase.I and show antileukemic and anti-tumor activity.

4 Claims, 3 Drawing Sheets

OTHER PUBLICATIONS

*J. Medicinal Chemistry*, (1990), 33, 972–978, "Plant Antitumor Agents. 29.[1] Synthesis And Biological Activity Of Ring D And Ring 3 . . . " Nicholas et al.

J. Org. Chem. (1974), 39, 303–311, "Synthesis Of Some DE And CDE Ring Analogs Of Camptothecin", Plattner et al.

J. Of Am. Chem. Soc. (1972), 94, 8615, "Synthesis Of Some DE And CDE Ring Analogs Of Camptothecin" Plattner et al.

*J. Org. Chem.*, (1974), 39, 3430–3432, "Synthesis Of Biological Evaluation Of DE–AB–Camptothecin", Danishefsky et al.

Govindachari et al, 453–454, "9–Methoxycamptothecin. A New Alkaloid From *Mappia foetida* Miers".

*Huaxue Xuebao*, (1984), 42, 42–50, "Mass Spectrometric Study Of Camptothecin And Related Compounds", Yang et al.

*Hua Hsueh Hsueh Pao* (1975), 33, 71–74, "Studies On The Derivatives Of Camptothecin", Pan et al.

*Cancer Treat. Rep.*, (1987), 71, 341–348, "Action Of 7–Ethylcamptothecin On Tumor Cells And Its Disposition In Mice", Nagata et al.

*Mol. Cell. Biol.*, (1987), vol. 7, 141–148, "Localization Of Specific Topoisomerase I Interactions Within The Transcribed Region Of Active Heat . . . ", Gilmour et al.

*Hua Hsueh Hsueh Pao*, (1977), 35, 193–200, "Chemical Consistuents Of The Anticancer Plant *Camptotheca acuminate* Decne. II . . . " Hsu et al.

*Chem. Ber.*, (1978), 111, 3403–3411, "Total Synthesis Of 7–Methoxycamptothecin", Baxmann et al.

*Hua Hsueh*, (1977), 2, 51–54, "Studies On The Constituents Of *Camptotheca acuminate* Done. I . . . " Tien et al.

*J. Nat. Prod*, (1979), 42, 475–477, "Plant Anticancer Agents. X. Isolation Of Camptothecin And 9–Methoxycamptothecin From Ervatamia . . . " Gunasekera et al.

*Chung–Kuo Yao Li Hsueh Pai*, (1980), 1, 109–112, "Distribution And Excretion Of Camptothecin Suspension And Sodium Camptothecin In Mice", Chen et al.

*Heterocycles*, (1980), 14, 951–953, "A Facile Synthesis Of (+)–Camptothecin By Enamine Annelation," Kametani et al.

*Hua Hsueh Hsueh Pai*, (1981), 39, 171–178, "Total Synthesis Of DI–10–Hydroxycamptothecin And DI–1-0–Methoxycamptothecin", Cai et al.

*Heterocycles*, (1981), 16, 1713–1717, "A Selective One–Step Introduction Of Hydroxylic Functions At The C–5 And C–7 Positions Of . . . ", Miyasaka et al.

*Yaoxue Xuebao*, (1984), 19, 63–68, "Studies On Polyphase Liposome Of Camptothecin", PL–CSA:, Luo et al.

*Aichi Ika Daigaku Igakkai Zasshi*, (1983), 11, 286–293, "Effects On An Antitumor Alkaloid, Camptothecin And Its Derivatives On Cell Growth . . . " Nagata et al.

*Biochem. Pharmacol*, (1985), 34, 1225–1230, "Action Of Camptothecin And Its Derivatives On Deoxyribonucleic Acid", Fukada.

*Proc Annu. Meet. Am Assoc. Cancer Res*, (1988), 29, A1080, "Structure–Activity Study Of The Relation Between Topoisomerase I Inhibition And Antitumor . . . ".

*Proc. Annu. Meet. Am Assoc. Cancer Res*, (1989), 8, A1019, "A Clinical Study Of A Camptothecin Derivative, CPT–11 On Hematological Malignancies", (MTG Abstract).

*Proc. Ann. Meet. Am Assoc. Cancer Res*, (1989), 30, A2485, "Irreversible Trapping Of The DNA–Topoisomerase I Covalent Complex And Affinity Labeling Of . . . ".

*Yao Hsueh Hsueh Pao*, (1988), 23, 186–188, "A New Alkaloid–19–Hydroxycamptothecin" Lin et al.

*J. Med. Chem*, (1989), 32, 715–720, "Modification Of The Hydroxy Lactone Ring Of Camptothecin: Inhibition Of Mammalian Topoisomerase I And . . . ", Mong et al.

*Science*, (1989), 246, 1046–1048, "DNA Topoisomerase I–Targeted Chemotherapy Of Human Colon Cancer In Xenografts", Giovanella et al.

*Proc. Annu. Meet. Am. Assoc. Cancer Res.*, (1989), A2476, "Structure–Activity Studies Of 20(S)–Captothecin Analogs" (Meeting Abstract).

a) DMF, K$_2$CO$_3$, 45°, 18h b) [structure: methyl acrylate] 45°, 72h c) CONCD HCl, GLACIAL HOAc, REFLUX, 2h d) ETHYLENE GLYCOL, CH$_2$Cl$_2$, Me$_3$SiCl, RT, 65h e) (EtO)$_2$CO, EtOH, KH, OMe, REFLUX, 3h f) KOtBu, EtI, DME, −78°C ⟶ RT, 18h g) Ac$_2$O, GLACIAL HOAc, H$_2$ (50psi), RANEY NICKEL, 45°, 6h h) Ac$_2$O, HOAc, NaNO$_2$, 0°, 2h i) CCl$_4$, REFLUX, 8h j) K$_2$CO$_3$, MeOH, O$_2$, RT, 24h k) 2N H$_2$SO$_4$, DME, REFLUX, 24h

CAMPTOTHECIN ANALOGS AS POTENT INHIBITORS OF TOPOISOMERASE I

RELATED APPLICATIONS

This is a division of application Ser. No. 07/600,825, filed Oct. 22, 1990 now U.S. Pat. No. 5,244,90, which is a continuation-in-part of Ser. No. 07/424,910, filed Oct. 23, 1989 now U.S. Pat. No. 5,106,741, which is a continuation-in-part of Ser. No. 07/043,449, filed Mar. 31, 1987 now U.S. Pat. No. 4,894,456, and a continuation-in-part of Ser. No. 07/511,953, filed Apr. 17, 1990 now U.S. Pat. No. 5,053,512, which is a continuation of Ser. No. 07/038,157, filed Apr. 14, 1987, now abandoned.

BACKGROUND OF THE INVENTION

1. Field of the Invention

The invention relates to camptothecin and analogs thereof which show life prologation effects in various leukemia systems such as P-388 and L-1210; inhibition of animal tumors such as B-16 melanoma and are potent inhibitors of topoisomerase I and a method of synthesizing the same by means of a novel hydroxyl-containing tricyclic intermediate. The invention also relates to a method for inhibiting topoisomerase I and treating colorectal cancer.

2. Discussion of the Background

Camptothecin is a pentacyclic alkaloid initially isolated from the wood and bark of *Camptotheca acuminata* by Wall et al (M. E. Wall, M. C. Wani, C. E. Cook, K. H. Palmer, A. T. McPhail, and G. A. Sim, *J. Am. Chem. Soc.*, 94, 388 (1966).

Camptothecin is highly biologically active and displays strong inhibitory activity toward the biosynthesis of nucleic acids. Additionally, camptothecin exhibits potent anti-tumor activity against experimentally transplanted carcinoma such as leukemia L-1210 in mice or Walker 256 tumor in rats.

Several methods for the synthesis of camptothecin and camptothecin analogs are known. These synthetic methods include (i) methods in which naturally occurring camptothecin is synthetically modified to produce a number of analogs and (ii) totally synthetic methods.

U.S. Pat. Nos. 4,604,463; 4,545,880; and 4,473,692 as well as European Patent Application 0074256 are examples of the former type of synthetic strategy. Additional examples of this strategy can be found in Japanese Patents 84/46,284; 84/51,287; and 82/116,015. These methods require naturally occurring camptothecin which is difficult to isolate and hence these methods are not suitable for the production of large quantities of camptothecin or analogs.

Examples of a variety of totally synthetic routes to camptothecin and camptothecin analogs can be found in the following references: *Sci Sin.* (*Engl. Ed*), 21(1), 87–98 (1978); *Fitoterpapia*, 45(3), 87–101 (1974); *Yakugaku Zashi*, 92(6), 743–6 (1972); *J. Org. Chem.*, 40(14), 2140–1 (1975); *Hua Hsueh Hsueh Pao*, 39 (2), 171–8 (1981); *J. Chem. Soc.*, Perkin Trans 1, (5), 1563–8 (1981); *Heterocycles*, 14 (7), 951–3 (1980); *J. Amer. Chem. Soc.*, 94(10), 3631–2 (1972); *J. Chem. Soc. D*, (7), 404 (1970) and U.S. Pat. No. 4,031,098.

Wani et al, *J. Med. Chem.*, 23, 554 (1980) discloses a synthesis of camptothecin and camptothecin analogs which involves the reaction of a tricyclic compound with a suitably substituted orthoaminoaldehyde to yield desoxycamptothecin as shown in Equation 1 below.

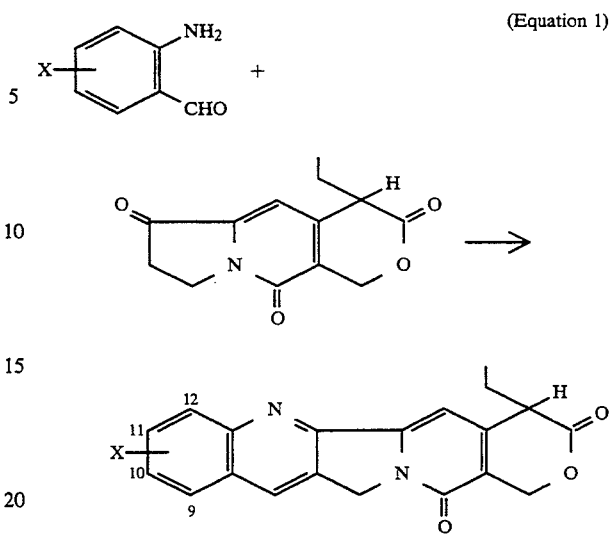

(Equation 1)

Desoxycamptothecin is then treated with oxygen to give camptothecin analogs. A major disadvantage of this procedure is the insolubility of desoxycamptothecin and its analogs, requiring large solvent volumes in the final step. A poor yield of the oxygenation product results under these conditions.

There exists a need, therefore, for a high-yield, efficient synthesis of camptothecin and camptothecin analogs which does not require prior isolation of naturally occurring camptothecin.

A need also exists for a method of synthesizing camptothecin and camptothecin analogs which does not suffer from insolubility problems of intermediate compounds and the resulting low yields.

A further need exists for new camptothecin analogs which can be synthesized in an efficient, high-yield manner and which show good biological activity.

SUMMARY OF THE INVENTION

Accordingly, one object of the present invention is to provide a method of synthesizing camptothecin and camptothecin analogs in high yield in a totally synthetic process.

Another object of the present invention is to provide a process for synthesizing camptothecin and camptothecin analogs which does not suffer from problems associated with the insolubility of intermediate compounds.

A further object of the invention is to provide a process for the preparation of camptothecin and camptothecin analogs which can be easily modified to produce a variety of analog structures.

Still a further object of the present invention is to provide camptothecin analogs which show good antitumor activity and other desirable biological activities.

A further object of the present invention is to provide a method for treating colorectal cancer by administering an antitumor or anticancer amount of a camptothecin compound.

These objects and other objects of the present invention which will become apparent from the following specification have been achieved by the present method for the synthesis of camptothecin and camptothecin analogs, which includes the steps of:

cyclizing a compound of the formula shown below, wherein X is an organic group which is converted to a carbonyl group when treated with an acid,

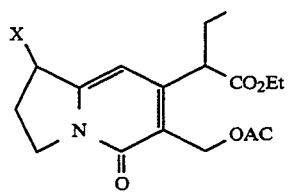

to form a lactone having the formula

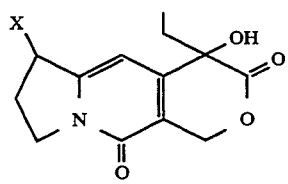

deprotecting said lactone to form a hydroxyl-containing tricyclic compound having the formula shown below, and

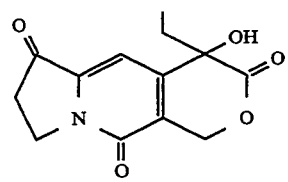

reacting said hydroxyl-containing tricyclic compound with a substituted ortho-amino compound of the formula

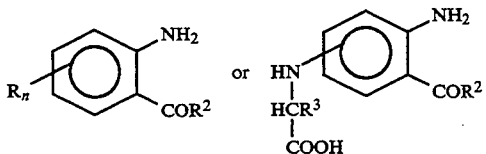

wherein n 1-2 and wherein each R is selected from the group consisting of cyano, methylenedioxy, formyl, hydroxy, $C_{1-8}$ alkoxy, nitro, amino, chloro, bromo, iodo, fluoro, $C_{1-8}$ alkyl, trifluoromethyl, aminomethyl, azido, amido and hydrazino groups; $R^2$ is $H_1$ or $C_1$ alkyl; and $R^3$ is the side-chain of any of the twenty naturally occurring amino acids.

DETAILED DESCRIPTION OF THE PREFERRED EMBODIMENTS

Figure 1A:
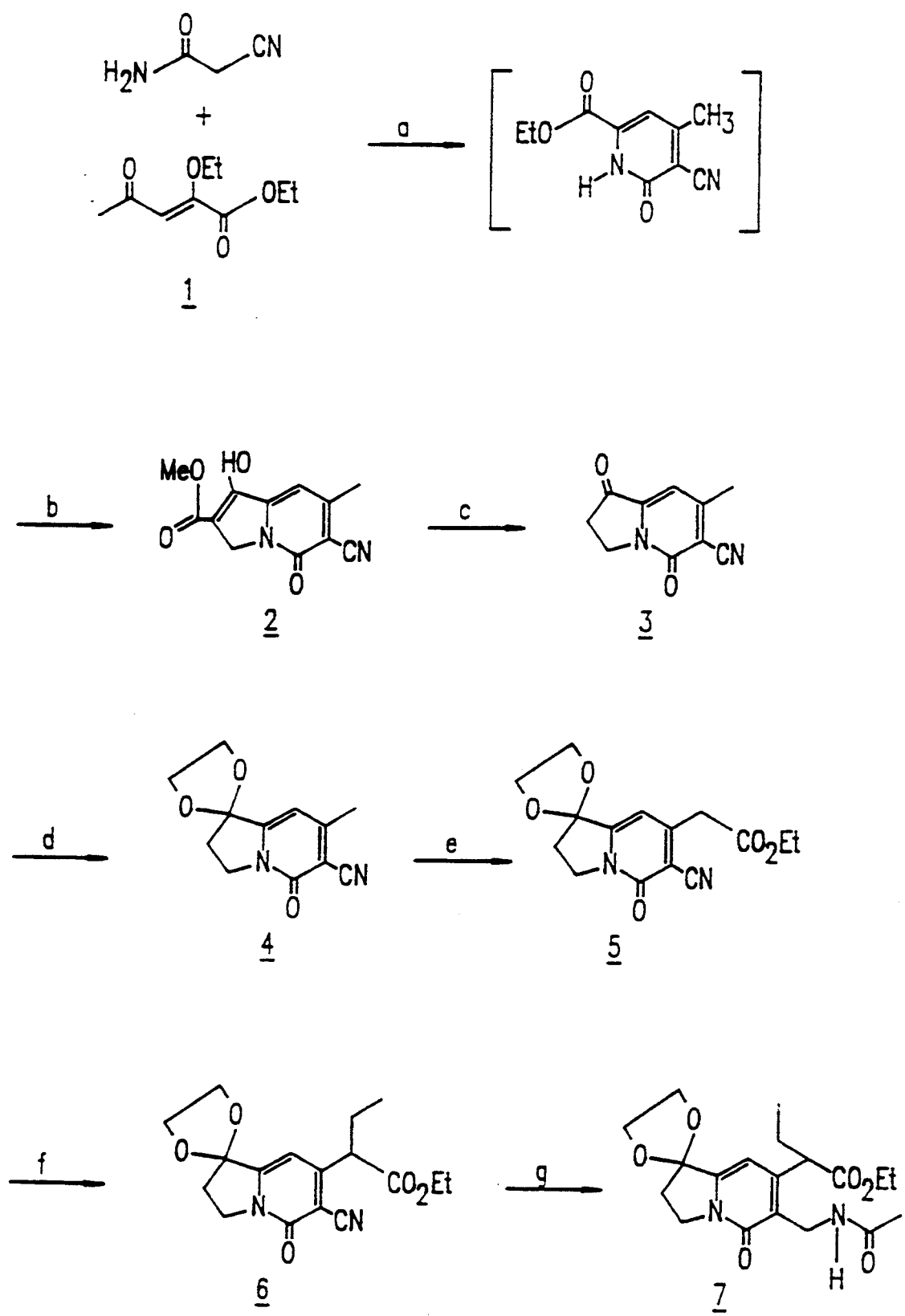
FIGS. 1a and 1b illustrates the synthesis of the hydroxyl-containing tricyclic compound 11, according to the invention.

The camptothecin analogs of the present invention have the basic camptothecin structural framework shown below in which the A ring is substituted.

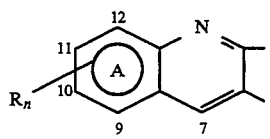

Substituents within the scope of the present invention include hydroxy, nitro, amino, chloro, bromo, iodo, fluoro, $C_{1-8}$ alkyl, $C_{1-8}$ alkoxy, trifluoromethyl, aminomethyl, amido, hydrazino, azido, formyl, and cyano groups as well as groups comprising amino acids bonded to the aromatic ring via the amino-nitrogen atom. Preferred alkyl groups include methyl, ethyl, propyl, butyl, isopropyl, isobutyl and sec-butyl groups. Preferred alkoxy groups include methoxy, ethoxy, propoxy and isopropoxy groups.

The preferred amino acid groups are the 20 naturally occurring amino acids having an (L) configuration. These amino acids are well known to those skilled in the art.

Additionally, two substituents on the A ring may be joined together to form a bifunctional substituent such as the methylenedioxy group. Methylenedioxy substituents may be bonded to any two consecutive positions in the A ring, for example, the 9,10; 10,11 or 11,12 positions.

Preferred substituents include the hydroxy, amino, cyano and methylenedioxy substituents. A particularly preferred substituent is the methylenedioxy group.

Particularly preferred compounds within the scope of the invention include 11-methoxy-20(RS)-camptothecin, 11-methoxy-20(S)-camptothecin, 11-hydroxy-20(RS)-camptothecin, 11-hydroxy-20(S)-camptothecin, 10-hydroxy-20(RS)-camptothecin, 10-hydroxy-20(S)-camptothecin, 9-methoxy-20(RS)-camptothecin, 9-methoxy-20(S)-camptothecin, 9-hydroxy-20(RS)-camptothecin, 9-hydroxy-20(S)-camptothecin, 10-nitro-20(RS)-camptothecin, 10-nitro-20(S)-camptothecin, 10-amino-20(RS)-camptothecin, 10-amino-20(S)-camptothecin, 9-nitro-20(RS)-camptothecin, 9-nitro-20(S)-camptothecin, 9-amino-20(RS)-camptothecin, 9-amino-20(S)-camptothecin, 11-nitro-20(RS)-camptothecin, 11-nitro-20(S)-camptothecin, 11-amino-20(RS)-camptothecin, 11-amino-20(S)-camptothecin, 10,11-dihydroxy-20(RS)-camptothecin, 10,11-dihydroxy-20(S)-camptothecin, 10-chloro-20(RS)-camptothecin, 10-chloro-20(S)-camptothecin, 10-methyl-20(RS)camptothecin, 10-methyl-20(S)-camptothecin, 11-formyl-20(RS)-camptothecin, 11-formyl-20(S)-camptothecin, 11-cyano-20(RS)-camptothecin, 11-cyano-20(S)-camptothecin and 10,11-methylenedioxy-20(RS)-camptothecin and 10,11-methylenedioxy-20(S)-camptothecin.

All structures in this application are understood to represent all possible isomers having the chemical structure indicated. The camptothecin structure shown above, therefore, represents compounds having the 20(S), 20(R) and 20(RS) configurations at the 20-position in the lactone ring. All such isomers and isomers arising from stereochemical configurations in the substituent group R are considered to be within the scope of the present invention.

The 20(RS)-camptothecin compounds of the present invention can be resolved into separate 20(R) and 20(S) enantiomers using known resolution processes. For example, 20(RS)-camptothecin derivatives can be resolved by reaction with a suitable chiral amine, such as R-(+)-α-methyl benzylamine or S-(-)-e-methyl benzylamine to form the corresponding diastereomeric amides by the method disclosed in US application serial number 07/511,953 incorporated herein by reference. After separation of the diastereomeric amides, the amides are treated with acid to reform the complete camptothecin ring structure.

Also included within the scope of the present invention are compounds in which the A ring of the camptothecin structure is modified to contain a hetero atom. The modified structures can have an A ring which contains 5 or 6 atoms and the hetero atom may be a nitrogen, sulfur or oxygen atom. These compounds may be represented by the general structure shown below in which the A ring is an aromatic 5 or 6 membered ring containing the hetero atom X.

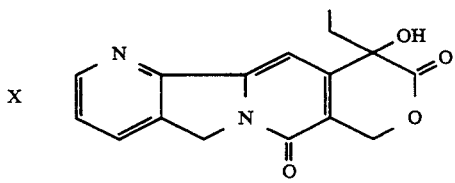

Preferred compounds having a modified A ring structure include compounds in which the A ring is a 6 membered nitrogen-containing aromatic ring and compounds in which the A ring is a 5 membered sulfur-containing aromatic ring. Particularly preferred compounds are 10-aza-20(RS)- and 10-aza-20(S)-camptothecins and A-nor-9-thia-20(RS)- and A-nor-9-thia-20(S)-camptothecins.

The camptothecin analogs noted above may be synthesized according to the method of the present invention by reacting a tricyclic compound containing a 20-hydroxyl group with an appropriately substituted ortho-amino aromatic aldehyde or ketone. Camptothecin analogs having an alkyl substituent on $C_7$ are produced when the appropriate ortho-amino ketone is used.

An important step in the method of the present invention is the synthesis of the hydroxyl-containing tricyclic compound having the formula shown below and in which $R^1$ is a hydroxyl group.

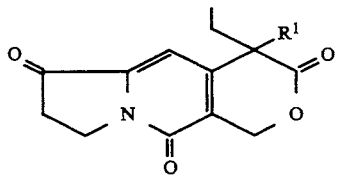

A synthetic method previously developed by the present inventors (J. Med. Chem., 23, 554 (1980)) utilized a related but structurally different tricyclic compound (formula I, $R^1 = H$). In that method, the tricyclic compound was reacted with a suitable orthoaminoaldehyde under alkaline or acidic conditions to yield a desoxycamptothecin. The desoxycamptothecin was then reacted with oxygen to give camptothecin analogs in which R is OH. A major disadvantage of this procedure is the insolubility of the desoxycamptothecin and its analogs, requiring large solvent volumes in the final step and giving poor yields of the oxygenation product.

Figure 1A:
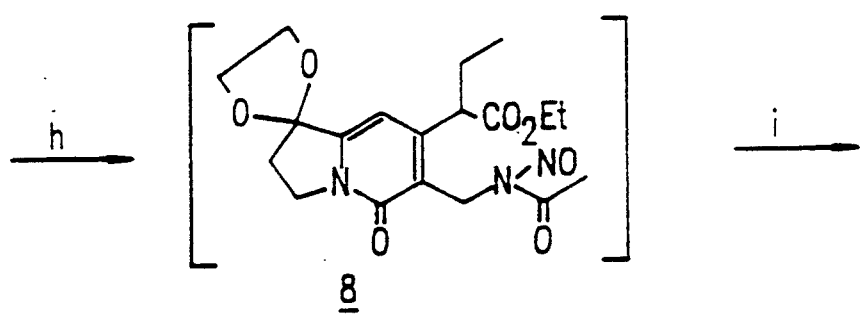
Figure 1A:
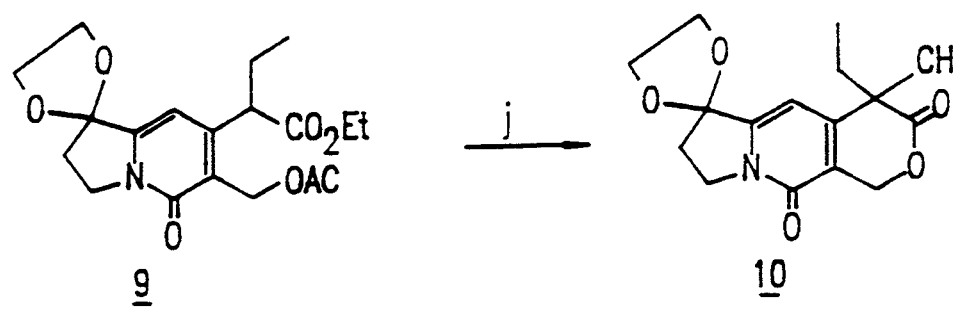
Figure 1A:
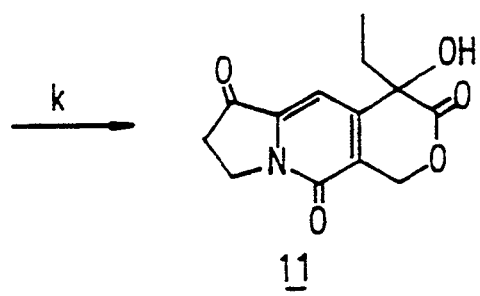
Figure 1B:
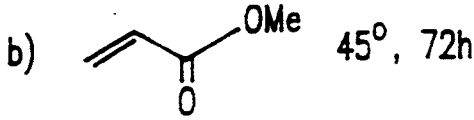

In contrast, the method of the present invention synthesizes the key tricyclic intermediate (11) according to FIG. 1. The synthesis of compounds 1-9 was disclosed in Wani et al, J. Med. Chem., 23, 554 (1980). In further contrast to the previous synthesis, the present method introduces the 20-hydroxyl group earlier in the synthetic sequence and then forms the lactone ring to give compound 10. After deprotection of the carbonyl group, the key hydroxyl-containing tricyclic compound 11 is obtained.

The protection of the carbonyl group in compound 3 can be performed using any appropriate organic protecting group which can be removed or converted into a carbonyl group upon treatment with acid. The carbonyl group is thereby "deprotected". These protecting groups are well known to those familiar with synthetic chemistry, and include acetals, ketals, thioacetals, thioketals, etc. Preferred protecting groups have 2-6 carbon atoms. An especially preferred protecting group is —OCH₂CH₂O—.

As a consequence of prior introduction of the hydroxyl group into the tricyclic compound 11, the desired pentacyclic analogs are reduced in one step by reaction with the appropriate ortho-amino carbonyl compounds. Both compound 11 and the corresponding ketonic synthons are very soluble in organic solvents whereas the pentacyclic product is insoluble. Hence, the oxygenation step, i.e, the introduction of the hydroxyl group, is conveniently carried out at the tricyclic stage rather than on the insoluble pentacyclic desoxy analogs.

Tricyclic compound 11 is then reacted with a suitably substituted ortho-amino aldehyde or ketone to give a camptothecin analog. Substituted ortho-amino aldehydes and ketones within the scope of the present invention include ortho-amino aldehydes and ketones having at least one additional substituent on the aromatic ring. This substituent may be at one or more of the positions equivalent to the 9, 10, 11 or 12 positions of the A ring of the final camptothecin structure as shown below.

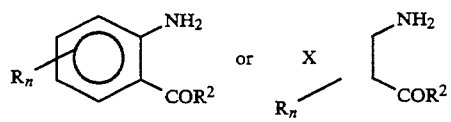

Preferred substituted ortho-amino aldehydes and ketones have substituents in one or more of the equivalent 9, 10, or 11 positions.

The substituents on the substituted ortho-aminoaldehyde or ketone include hydroxy, nitro, amino, $C_{1-8}$ alkyl, chloro, bromo, iodo, fluoro, methylenedioxy (—O—CH₂O—), $C_{1-8}$ alkoxy, trifluoromethyl, aminomethyl, amido, hydrazino, azido, formyl, and cyano groups as well as groups comprising amino acids bonded to the aromatic ring through the amino-nitrogen atom. Preferred examples include the hydroxy, amino, cyano and methylenedioxy substituents. A particularly preferred substituent is the methylenedioxy group.

When an ortho-amino ketone is reacted with tricyclic compound 11, a camptothecin analog having an alkyl substituent at $C_7$ is produced. Preferred ortho-amino ketones are those in which $R^2$ is an alkyl group having 1-8 carbon atoms. Especially preferred ortho-amino ketones are ortho-aminoacetophenone and ortho-aminopropiophenone.

The ortho-amino aldehydes and ketones may be substituted by a group having the formula

—NH—CHR³—COOH wherein $R^3$ is a side-chain of one of the twenty naturally occurring amino acids. The amino acid substituent is bonded to the aromatic ring via the nitrogen atom and may be bonded to any position on the aromatic ring equivalent to the 9, 10, 11 or 12 positions of the A ring of the final camptothecin structure.

The ortho-amino aldehydes and ketones may be in the free carbonyl form or in a form in which the carbonyl of the aldehyde or ketone is protected by a standard protecting group. These protecting groups are well known to those skilled in the art. Ortho-amino aldehydes and ketones in the free carbonyl form and in the protected carbonyl form are considered within the scope of the present invention and are suitable for use in the present method.

The reaction in which the hydroxyl group is introduced into the tricyclic intermediate compound, i.e, the cyclizing step, can be effected by any suitable reaction which will introduce the hydroxyl group at the appropriate position of compound 9 without causing significant side reactions such as degradation of compound 9 itself.

The reaction is preferably conducted in the presence of a basic catalyst. Suitable basic catalysts include both inorganic and organic bases. Preferred inorganic bases include, for example, sodium and potassium carbonate and sodium and potassium bicarbonate. Preferred organic bases include hindered bases such as triethylamine and diisopropylamine. A particularly preferred basic catalyst is potassium carbonate.

The reaction in which the hydroxyl group is introduced can be performed in the presence of any polar or non-polar solvent in which the reactants are suitably soluble to react. Preferred are polar organic solvents such as methanol, ethanol, propanol, butanol and dimethylformamide. Ether solvents, including crown ethers may also be used.

The oxygen of the hydroxyl group is generally derived from molecular oxygen which is bubbled through the reaction solution. Although the use of oxygen is preferred, other sources of oxygen, such as air, may also be used. Other oxidizing agents such as hydrogen peroxide, lead tetraacetate and selenium dioxide may also be employed.

This reaction is preferably conducted at room temperature although the specific reaction temperature will be dependent on the specific reaction conditions and reactants used.

The deprotection of the carbonyl group in compound 10 is accomplished by treatment with acid. Suitable acids include mineral acids such as HCl, $H_2SO_4$, $HNO_3$, and $H_3PO_4$, as well as organic acids such as alkanoic acids having 1-10 carbon atoms, preferably acetic acid, and $C_{1-12}$ arylsulfonic acids, especially p-toluenesulfonic acid. The deprotection of a carbonyl group in this manner is well known to those skilled in the art.

The tricyclic compound 11 is then reacted with a substituted ortho-amino aldehyde or ketone in the presence of an acid or base catalyst. The base catalyst is preferably any of the base catalysts noted above in cyclizing compound 9 to form compound 10, i.e., for the introduction of the hydroxyl group into tricyclic compound 11. The acid catalyst is preferably a mineral acid such as for example HCl, $H_2SO_4$, $HNO_3$, and $H_3PO_4$, or organic acids such as $C_{1-8}$ alkanoic acids and $C_{1-12}$ arylsulfonic acids, especially p-toluenesulfonic acid.

The reaction of compound 11 with an appropriate ortho-amino compound may be carried out neat or in the presence of a polar or non-polar solvent. Preferred polar solvents are the $C_{1-6}$ alcohols, ethers and dimethylformamide. Preferred non-polar solvents are branched or straight-chained alkyl hydrocarbons having 4-10 carbon atoms and aromatic hydrocarbons having 6-20 carbon atoms. An especially preferred solvent is toluene.

The reaction of the hydroxyl-containing tricyclic compound with the optionally substituted ortho-amino compound is generally conducted with heating at reflux. Reaction times will vary depending on the particular reactants but are generally in the range from about 10 minutes to 24 hours. Preferred reaction times are in the range of 2-10 hours.

Also within the scope of the present invention are camptothecin analogs prepared by hydrolyzing the lactone ring of the camptothecin analogs prepared as described above using an aqueous alkali solution to prepare the alkali metal salts of camptothecin analogs in which the lactone ring has been opened to form the corresponding hydroxyl and carboxylate functional groups. The hydrolysis is typically carried out in aqueous solution using one equivalent of an alkali metal hydroxide. Preferred alkali metal hydroxides are potassium hydroxide and sodium hydroxide, with sodium hydroxide being particularly preferred.

The hydrolysis reaction may be conducted at any temperature which allows adequate reaction of the camptothecin analog and the aqueous alkali metal hydroxide so long as the temperature is sufficiently low to prevent decomposition of the starting materials. Suitable temperatures are from about 5°-50° C. with preferred temperatures being approximately room temperature. After hydrolysis, the metal salt of the camptothecin analog may be isolated and purified by standard recrystallization or chromatographic processes. Particularly preferred salts are the sodium salts of 10,11-methylenedioxy-20(RS)-camptothecin and 10,11-methylenedioxy-20(S)-camptothecin.

The camptothecin analogs of the present invention have excellent biological activity. As used herein, "biological activity" refers to the ability of the camptothecin analogs to inhibit topoisomerase enzymes, in particular topoisomerase I, and their ability to exert anti-leukemic activity. Anti-leukemic activity may be determined by the ability of the respective compounds to inhibit L-1210 mouse leukemia cells. Anti-leukemic activity is demonstrated in Tables I-III by the activity of the particular compounds against L-1210 mouse leukemia cells. Other known anti-leukemic and anti-tumor in vitro and in vivo models, such as the clearable complex assay shown in Table IV may be used as well to determine anti-leukemic activity.

Camptothecin analogs, in particular 9-amino-, 10-amino-, 10,11-methylenedioxy- and the sodium salt of 10,11-methylenedioxy-camptothecin having both the 20(RS) and 20(S) configurations are highly active as topoisomerase I inhibitors as shown in in vitro assays and also in in vivo tumor models such as human colorectal xenograft tumor lines. These camptothecin analogs have been shown to cause remission of tumors in human colorectal xenograft lines such as human colon cancer HT-29, colon cancer CASE and SW 48 tumors.

See B. C. Giovanella, J. S. Stehlin, M. E. Wall, M. C. Wani, A. W. Nicholas, L. F. Liu, R. Silber and M. Potmesil, Highly Effective DNA Topoisomerase-I Targeted Chemotherapy of Human Colon Cancer in Xenografts, Science, vol 246, pages 1046–1048 (1989). In addition, certain human liver and lung xenografts are strongly inhibited by these analogs.

The camptothecin analogs of the present invention, and in particular 9-amino-20(S)-, 10-amino-20(S)-, 10,11-methylenedioxy-20(S)- and the sodium salt of 10,11-methylenedioxy-20(S)camptothecin, therefore, provide a method of inhibiting topoisomerase I and treating colorectal cancer by administering to a mammal, and in particular a human patient, an anti-tumor effective amount of the camptothecin analog. The high antitopoisomerase I activity of these camptothecin analogs will allow the treatment of colon and rectal adenocarcinomas in mammals. Similarly, these compounds may be useful for treating liver and lung neoplasms.

The mouse anti-leukemic activity of the various ring A oxygenated camptothecin analog is shown in Table I. Similar data for nitrogen analogs and for ring A modified analogs are shown in Tables II and III, respectively. In most cases camptothecin or an analog with well-defined activity was also assayed at the same time as a positive control, and the data are shown in the table footnotes. In this manner the relative antileukemic activity of the various compounds can be compared. The biological activity of additional camptothecin analogs is described in J. Med. Chem., 23, pages 554–560 (1980).

The ability of camptothecin to inhibit topoisomerase I has been shown. See J. Biol. Chem., 260, 14873-73 (1985).

TABLE I

Comparative Activities and Potencies of Ring A Oxygenated Camptothecin Analogues in Mouse Leukemia Assay[a,b]

| Camptothecin derivative | max % T/C (dose, mg/kg) | no. cures out of 6 | $K_E{}^c$ at max % T/C | active dose range, mg/kg | toxic dose, mg/kg |
|---|---|---|---|---|---|
| 10-OH-20(S)[a,d] | 297 (3.1) | 0 | | $0.4^3$–3.1 | 6.25 |
| 10-OMe-20(S)[a,d] | 167 (1.6) | 0 | | $0.4^3$–1.6 | 3.1 |
| 11-OH-20(RS)[b,f] | 357 (60.0) | 3 | J 5.68 | $7.5^e$–60.0[g] | >60.0 |
| 10,11-diOMe-20(RS)[b,h] | inactive | | | | >50.0 g |
| 10,11-OCH$_2$O-20(RS)[b,i] | 325 (2.0) | 2 | J 5.97 | $2.0^e$–4.0 | >8.0 |
| 10-OCH$_2$CO$_2$Na-20(S)[a,d] | inactive | | | | |
| 10-Et$_2$N(CH$_2$)$_2$O-20 (S)[a,d] | 183 (16.0) | 0 | | $2.0^e$–32.0[g] | >32.0 |

[a]Denotes testing in P-388 system; treatment schedule QO4DX03; % T/C = survival time of treated/control animals × 100; IP using Klucel emulsifier.
[b]Denotes testing in L-1210 system; treatment schedule QO4DXO2; % T/C - survival time of treated/control animals × 100; IP using Klucel emulsifier.
[c]Log$_{10}$ of initial tumor cell population minus log$_{10}$ of tumor cell population at end of treatment.
[d]20(S)-Camptothecin and 20(S)-camptothecin sodium were used as reference standards; for 20(S)-camptothecin, % T/C (4.0 mg/kg) = 197; for 40(S)-camptothecin sodium, % T/C (40.0 mg/kg) = 212.
[e]Lowest dose administered.
[f]20(S)-camptothecin and 20(S)-camptothecin sodium were used as reference standard: for 20(S)-camptothecin, % T/C (8.0 mg/kg) = 164; for 20(S)-camptothecin sodium, % T/C (40.0 mg/kg) = 178.
[g]Highest dose administered.
[h]20(S)-camptothecin sodium was used as a reference standard: % T/C (25.0 mg/kg) = 206.
[i]20(S)-camptothecin was used as a reference standard: % T/C (5 mg/kg) = 166.

TABLE II

Comparison of Activities and Potencies of Ring A Nitrogen Substituted and Ring A Nitrogen/Oxygen Disubstituted Analogues in L-1210 Mouse Leukemia Assays[a]

| Camptothecin derivative | max % T/C (dose, mg/kg) | no. cures out of 6 | $K_E{}^c$ at max % T/C | active dose range, mg/kg | toxic dose, mg/kg |
|---|---|---|---|---|---|
| 10-NO$_2$-20(RS)[c] | 219 (15.5) | 1 | J 5.86 | $7.5^d$–15.5 | 31.0 |
| 10-NH$_2$-20(RS)[c] | 329 (8.0) | 3 | J 5.86 | $4.0^d$–16.0 | 32.0 |
| 10-NHAc-20(RS)[c] | 318 (40.0) | 1 | J 5.86 | $5.0^d$–40.0[e] | >40.0 |
| 9-NO$_2$-20(S)[f] | 348 (10.0) | 5 | J 5.86 | $2.5^d$–20.0 | 40.0[e] |
| 12-NO$_2$20(S)[f] | 151 (40.0) | 0 | 0.34 | $2.5^d$–40.0[e] | >40.0 |
| 9-NH$_2$-20(S)[f] | 348 (2.5) | 4 | J 5.86 | $2.5^d$–5.0 | 10.0 |
| 12-NH$_2$-20(S)[f] | inactive | | | | |
| 9-NO$_2$-10-OMe-20(S)[f] | 160 (40.0) | 0 | 1.03 | $2.5^d$–40.0[e] | >40.0 |
| 9-NH$_2$-10-OMe-20(S)[f] | 186 (40.0) | 0 | 2.92 | $2.5^d$–40.0[E] | >40.0 |
| 9-NO$_2$-10-OH-20(S)[f] | 131 (20.0) | 0 | −1.12 | $2.5^d$–40.0[e] | >40.0 |
| 9-NHAc-10-OH-20(S)[f] | 220 (40.0) | 0 | 5.50 | $2.5^d$–40.0[e] | >40.0 |

[a]Treatment schedule QO4DX2; % T/C = survival time of treated/control animals × 100; IP using Klucel emulsifier.
[b]Log$_{10}$ of initial tumor cell population minus log$_{10}$ of tumor cell population at end of treatment.
[c]20(S)-Camptothecin (1) and 10-hydroxy-20(S)-camtothecin (2) were used as reference standards: for 1, % T/C (9.0 mg/kg) = 197; for 2, % T/C (24.0 mg/kg) = 230.
[d]Lowest dose administered.
[e]Highest does administered.
[f]Compounds 1 and 2 were used as reference standards: for 1, % T/C (10.0 mg/kg) = 267; for 2, % T/C (20.0 mg/kg) = 348.

TABLE III

Comparative Activities of Ring A Modified and Homologated Camptothecin Analogues in Mouse Leukemia Assays[a,b]

| Camptothecin derivative | max % T/C (dose, mg/kg) | no. cures out of 6 | $K_E{}^c$ at max % T/C | active dose range, mg/kg | toxic dose, mg/kg |
|---|---|---|---|---|---|
| 10-aza-10(RS)[1,d] | 162 (2.5) | 0 | 1.61 | $1.25^e$–2.5 | 5.0 |
| 12-aza-20(RS)[b,f] | 175 (32.0) | 0 | | 8.0–32.0 | >32.0 |

TABLE III-continued

Comparative Activities of Ring A Modified and Homologated Camptothecin Analogues in Mouse Leukemia Assays[a,b]

| Camptothecin derivative | max % T/C (dose, mg/kg) | no. cures out of 6 | $K_E^c$ at max % T/C | active dose range, mg/kg | toxic dose, mg/kg |
|---|---|---|---|---|---|
| A-nor-9-thia-20(RS)[a,d] | 193 (25.0) | 0 | −0.94 | 3.12[e]–25.0 | 50.0[g] |

[a]Denotes testing in L-1210 system; treatment schedule QO4DX2; % U/C survival time of treated/control animals × 100; IP using Klucel emulsifier.
[b]Denotes testing in P-388 system; treatment schedule QO4DX2; % T/C = survival time of treated/control animals × 100; IP using Klucel emulsifier.
[c]$Log_{10}$ of initial tumor cell population minus $log_{10}$ of tumor cell population at end of treatment.
[d]20(S)-Camptothecin sodium was used as a reference standard: % T/C (40.0 mg/kg) = 215.
[e]Lowest dose administered.
[f]20(S)-Camptothecin was used as a reference standard: % T/C (4.0 mg/kg) = 197.
[g]Highest does administered.

Table IV below shows the surprising topoisomerase I inhibitory activity of the camptothecin analogs of the present invention. The cleavable complex assay was performed according to the method described in Hsiang, Y-H et al, *J. Biol. Chem.*, 260:14873–14878 (1985),

TABLE IV

Cleavable Complex Assay of Camptothecin and Analogs

| Compound | Name* | $EC_{50}$** µg/mL |
|---|---|---|
| 1 | 10,11-MDO-20(S)-CPT | ~.01 µg/mL |
| 2 | 10,11-MDO-20(RS)-CPT | ~.02 µg/mL |
| 3 | 10,11-MDO-20(S)-CPT, Na+ SALT | ~0.1 µg/mL |
| 4 | 9-AMINO-20(RS)-CPT | ~0.2 µg/mL |
| 5 | 10,11-MDO-20(RS)-CPT, Na+ SALT | ~0.2 µg/mL |
| 6 | 20(S)-CPT | ~0.2 µg/mL |
| 7 | 20(RS)-CPT | ~0.8 µg/mL |
| 8 | 20(RS)-CPT, Na+ SALT | ~0.9 µg/mL |
| 9 | 9,10-MDO-20(RS)-CPT | ~2 µg/mL |
| 10 | 9-AMINO-20(RS)-CPT, Na+ SALT | ~10 µg/mL |
| 11 | 20(R)-CPT | >10 µg/mL |

*Abbreviations
CPT = Camptothecin
MDO = Methylenedioxy
**$EC_{50}$ is the concentration of a compound which gives 50% topoisomerase I inhibition as revealed by cleavable complex formation. All $EC_{50}$ values represent the mean of several independent assays; all values are normalized with respect to #6, 20(S)-CPT, which was always assayed as a control.

The clearable complex assay correlates well with in vivo anti-tumor activity in animal models for camptothecin analogs. See Hsiang et al, *Cancer Research*, 49:4385–4389 (1989) and Jaxel et al, *Cancer Research*, 49:1465–1469 (1989).

Tumor histioculture studies using human cancers obtained by surgery or biopsy are shown in Table V below. Inhibition of tumor cell proliferation was performed in vitro on human colorectal tumors obtained from surgery or biopsy as described by Vescio et al *Proc. Nat'l. Acad. Sci. USA*, 84:5029–5033 (1987), with the following modifications: Tumors were cultured 1 day prior to drug addition; tumors were exposed to compounds for 24 hours, washed, and then exposed to 3[H]thymidine for 3 days.

TABLE V

Human Colon Tumor Histioculture Inhibition of Cell Proliferation

| Name* | **$IC_{50}$ (µg/mL) |
|---|---|
| 20(S)-CPT | ~0.02 |
| 10,11-MDO-20(S)-CPT | ~0.003 |
| 10,11-MDO-20(S)-CPT, Na+ SALT | ~0.005 |
| 10,11-MDO-20(RS)-CPT | ~0.005 |
| 10,11-MDO-20(RS)-CPT, Na+ SALT | ~0.01 |

*Abbreviations
CPT = Camptothecin
MDO = Methylenedioxy
**$IC_{50}$: concentration of compound required to inhibit by 50% the incorporation of 3[H]thymidine into DNA In the tumor histioculture studies shown in Table V, the compounds of the present invention demonstrates significant activity, measured as inhibition of tumor cell proliferation during treatment with the compounds of the present invention. As used herein, the term "cancer" is synonymous with the terms "malignant tumor" and more generally "tumor". The data shown in Table V demonstrate the activity of the present compounds against human colon cancer, which is well known to be a very resistant cancer to chemotherapy. See H. L. Davis, Chemotherapy of Large Bowel Cancer, *Cancer (Phila.)* 50: 2638–2646 (1982); J. R. Neefe and P. S. Schein, Chapter 43: The Management of Disseminated Large-Bowel Cancer in *Principals of Cancer Treatment*, page 402, ed. S. K. Carter, E. Glatstein and R. B. Livingston, McGraw-Hill Co., 1982; K. Mekhail-Ishak, *Cancer Research*, 49: 4866–4869 (1989) and P. J. Ferguson and Y. C. Cheng, *Cancer Research*, 49: 1148–1153 (1989).

The compounds of the present invention exhibit anti-tumor activity against human colon cancer, which is known to exhibit de novo drug resistance, and thus be difficult to treat chemotherapeutically. Therefore, it is believed that the present compounds will be active against a wide spectrum of mammalian (including human) cancers such as cancers of the oral cavity and pharynx (lip, tongue, mouth, pharynx), esophagus, stomach, small intestine, large intestine, rectum, liver and biliary passages, pancreas, larynx, lung, bone, connective tissue, skin, breast, cervix uteri, corpus endometrium, ovary, prostate, testis, bladder, kidney and other urinary tissues, eye, brain and central nervous system, thyroid and other endocrine gland, leukemias (lymphocytic, granulocytic, monocytic), Hodgkin's disease, non-Hodgkin's lymphomas, multiple myeloma, etc. Obviously, the present compounds may be used to treat other cancers not specifically named so long as antitumor activity is demonstrated by the present compounds in the particular cancer.

Pharmaceutical compositions containing the novel camptothecin analogs are also within the scope of the present invention. These pharmaceutical compositions may contain any quantity of a camptothecin analog which is effective to inhibit topoisomerase I in vitro or in vivo or exhibit anti-leukemic activity in vivo. Mammals such as animals and humans are treatable with the inventive compositions. Typical in vivo doses within the scope of the invention are from about 0.1-100 mg of camptothecin per patient per day. A particularly preferred range is 1-40 mg/kg.

There may also be included as part of the composition pharmaceutically compatible binding agents, and/or adjuvant materials. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

One mode of administration of the compounds of this invention is oral. Oral compositions will generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.1% of active compound but may be varied depending upon the particular form.

The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

As known in this art, the dosage values will vary with the specific cancer to be treated, the stage of tumor development, tumor location, weight and physical condition of the patient being treated, etc. Good results should be achieved when the compounds described herein are administered to a subject requiring such treatment as an effective oral, parenteral or intravenous dose. It is to be understood that for any particular subject, specific dosage regimens should be adjusted to the individual need and the professional judgment of the person administering or supervising the administration of the aforesaid compound. It is to be further understood that the dosages set forth herein are exemplary only and they do not limit the scope or practice of the invention. Dosages above or below the range cited above are within the scope of the present invention and may be administered to the individual patient if desired and necessary. The dosages may be administered at once, or may be divided into a number of smaller doses to be administered at varying intervals of time.

The present invention also includes standard pharmaceutically acceptable acid and base addition salts of the camptothecin compounds of the present invention. Suitable acid addition salts are obtained by the addition of HCl, $H_3PO_4$, $H_2SO_4$, etc. or organic acids such as malic, maleic or tartaric acids. Suitable basic addition salts may be obtained by the addition amines, i.e., ammonium salts and quaternary ammonium salts formed with primary, secondary or tertiary amines in which the nitrogen atom of the amine contains 1, 2, or 4 lower alkyl or substituted lower alkyl groups. Substituted lower alkyl groups containing one or more hydroxy groups are preferred. Obviously, the present invention is not limited to these examples of acid and base addition salts and includes all acid and base addition salts which can be prepared using the camptothecin compounds of the present invention and which are pharmaceutically acceptable.

Other features of the invention will become apparent in the course of the following descriptions of exemplary embodiments which are given for illustration of the invention and are not intended to be limiting thereof.

EXAMPLES

SYNTHESIS OF TRICYCLIC COMPOUND 11

6-Cyano-7-methyl-1,5-dioxo-$\Delta^{6(8)}$-tetrahydroindolizine (Compound 3)

Ethyl acetopyruvate was prepared from acetone and diethyl oxalate as described in *Org. Synthesis*, Coll. Vol. 1, 238 (1958). Further reaction with triethylorthoformate and ammonium chloride in ethanol afforded the known enol ether 1. See L. Claisen, *Chem. Ber.*, 40, 3903 (1907).

Ethyl(2-ethoxy-4-oxo)-pent-2-enoate(1) (100.01 g, 0.538 mol) was added gradually to a preheated (45), mechanically stirred mixture of $K_2CO_3$ (79.04 g, 0.573 mol) and cyanoacetamide (48.46 g, 0.577 mol) in DMF (960) mL). The mixture was kept at 45° for 18 hr, whereupon the thick, red slurry was treated dropwise with freshly distilled methyl acrylate (360 mL, 343 g, 3.99 mol). After 72 hr at 45°, the red suspension was filtered, dissolved in 5 liters of water, and acidified to pH 1.5 with concentrated HCl. Crude bicyclic ester 2 (127.98 g) was collected by filtration as a pink solid. Without further treatment, 2 was refluxed in a solution concentrated of HCl (800 ml) and glacial HOAc (800 ml) for 2 hr. Removal of the solvents in vacuo gave the bicyclic pyridone 3 (39.66 g, 39% based on 1).

6-Cyano-1,1-(ethylenedioxy)-7-methyl-5-oxo-$\Delta^{6(8)}$-tetrahydroindolizine (Compound 4)

Compound 3 (10.54 g, 0.056 mol) as a stirred solution in $CH_2Cl_2$ (500 ml) was treated at room temperature under $N_2$ with ethylene glycol (6.85 ml, 7.63 g, 0.123 mol) and $Me_3SiCl$ (31.30 ml, 26.89 g, 0.247 mol) and left at ambient temperature (20°) for 65 hr. The solution was filtered to remove some black suspended material before washing with 1 M aq NaOH solution. The organic phase was washed with brine, filtered through Celite and evaporated to afford ethylene ketal 4 (10.26 g, 79%) as a pink solid.

6-Cyano-1,1-(ethylenedioxy)-7-[(ethoxycarbonyl)methyl]-5-oxo-$\Delta^{6(8)}$-tetrahydroindolizine (Compound 5)

The ketal 4 (5.0 g, 0.022 mol) was refluxed in a suspension of KH (11.9 g, 0.068 mol) in toluene (40 mL) for 10 min. Diethyl carbonate (6.79 g, 0.058 mol) and a catalytic amount (0.31 g, 6.7 mmol) of absolute ethanol were added and refluxing continued for 3 hr. The dark solid was crushed and the resulting suspended salt of 5 was collected by filtration. The salt was neutralized by the careful addition of cold aqueous HOAc. Water was added and the product extracted into $CH_2Cl_2$. Following a wash with brine and drying ($Na_2SO_4$), evaporation of the $CH_2Cl_2$ afforded crude 5. Purification by silica gel chromatography (2% MeOH in $CHCl_3$) and recrystallization (MeOH) gave pure 5 (4.97 g, 76%).

6-Cyano-1,1-(ethylenedioxy)-7-[1'(ethoxycarbonyl)propyl]-5-oxo-$\Delta^{6(8)}$-tetrahydroindolizine (Compound 6)

A stirred solution of the ester 5 (4.01 g, 0.0132 mol) in anhydrous DME (70 mL) at $-78°$ C. was treated with potassium tert-butoxide (1.7 g, 15 mmol). After 5 min, EtI (8.24 g, 0.053 mol) was added over a 5 min period. After stirring for 1.5 hr at $-78°$ C., the mixture was left to warm to room temperature overnight. Water was added and the product extracted into $CH_2Cl_2$. After washing with brine and drying ($Na_2SO_4$), $CH_2Cl_2$ was evaporated to give the ester 6 (4.3 g, 98%).

6-(Acetamidomethyl)-1,1-(ethylenedioxy)-7-[1'-(ethoxycarbonyl)propyl]-5-oxo-$\Delta^{6(8)}$-tetrahydroindolizine (Compound 7)

A solution of the ester ketal 6 (2.0 g, 6.0 mmol) in acetic anhydride (30 mL) and HOAc (10 mL) was hydrogenated for 6 hr at 45° C. under 50 psi in the presence of Raney nickel (3 g; washed with HOAC). The catalyst was removed by filtration and the solvent removed in vacuo to give 7 (2.3 g, 100%) as an oil. Purification by silica gel column chromatography (2% MeOH in $CHCl_3$) gave pure 7 as an oil.

6-(Acetoxymethyl)-1,1-(ethylenedioxy)-7-[1'-(ethoxycarbonyl)propyl]-5-oxo-$\Delta^{6(8)}$-tetrahydroindolizine (Compound 9)

A cooled solution of amide 7 (2.3 g, 6.0 mmol) in $Ac_2O$ (30 mL) and HOAc (10 mL) was treated with $NaNO_2$ (1.8 g, 26 mmol) and the reaction mixture stirred for 2 hr at 0° C. Inorganic salts were removed by filtration and the solvent removed in vacuo at room temperature to afford the N-nitroso intermediate 8 as an oil. Compound 8 was converted directly to the title acetoxy compound 9 by refluxing overnight in $CCl_4$. The solution was washed with water, dried ($Na_2SO_4$) and the solvent removed in vacuo to give 9 (2.3 g 100%) as an oil.

1,1'Ethylenedioxy-5-oxo-(5'-ethyl-5'-hydroxy-2'H,5'H,6'H-6-oxopyrano)-[3',4'-f]-$\Delta^{6(8)}$tetrahydroindolizine (Compound 10)

Oxygen was bubbled through a mixture of 6-(acetoxymethyl)-1,1-(ethylenedioxy)-7-[1'-ethoxycarbonyl)propyl]-5-oxo-$\Delta^{6(8)}$tetrahydroindolizine (Compound 9, 405 mg, 1.07 mmol), anhydrous $K_2CO_3$ (148 mg 1.07 mmol) and methanol (7.5 mL) for 24 hr. The solution was cooled in an ice bath and made acidic (pH 2–4) by addition of 1N $H_2SO_4$. Most of the methanol was removed in vacuo at room temperature, and water (20 mL) was added. The aqueous solution was extracted with $CH_2Cl_2$ (3×20 mL), dried ($NaSO_4$) and evaporated to give a solid which was crystallized from $CH_2Cl_2$-hexane to give 280 mg (85%) of 10: mp 179°–181° C.; $\nu_{max}$ ($CHCl_2$) 1740, 1660 $cm^{-1}$; $^1$H-NMR ($CCCl_3$) $\delta$ 0.91 (t, 3, J=7 Hz, $CH_2CH_3$), 1.75 (q, 2, J=7 Hz, $CH_2CH_3$), 2.35 (t, 2, J=6.5 Hz, $CH_2$ $\alpha$ to ketal), 4.1 (m, 6, $OCH_2CH_2O$ and $CH_2N$), 5.30 (m, 2, $ARCH_2O$), 6.87 (s, 1, pyridone). Anal. Calcd for $C_{15}H_{17}NO_6$: C, 58.63; H, 5.54; N, 4.56. Found: C, 58.72, H, 5.68; N, 4.57.

5'RS-1,5-Dioxo-(5'-ethyl-5'-hydroxy-2'H, 5'H, 6'H-6-oxopyrano) -[3',4', f]-$\Delta^{6(8)}$tetrahydroindolizine (Compound 11)

A solution of 10 (3.88 g, 12.6 mmol) in 2N $H_2SO_4$ (50 mL) and DME (50 mL) was heated for 24 hr under $N_2$. The reaction mixture was concentrated to one half its volume in vacuo, diluted with $H_2O$ (100 mL) and extracted with $CH_2Cl_2$ (5×50 mL). The organic layer was dried ($Na_2SO_4$) and evaporated to yield a solid which was crystallized from $CH_2Cl_2$-hexane to yield 2.68 g (80%) of 11 as a light brown solid: mp 185°–187° C.; $\nu_{max}$ ($CHCl_3$) 1750 (shoulder, ketone), 1745 (lactone), 1660 $cm^{-1}$ (pyridone); $^1$H-NMR ($CDCl_3$) $\delta$ 0.91 (t, 3, J=7 Hz, $CH_2CH_3$), 1.80 (q, 2, J=7 Hz, $CH_2CH_3$), 2.93 (t, 2, J=6.5 Hz, $CH_2C=O$), 4.30 (t, 2, J=6.5 Hz, $CH_2N$), 5.35 (m, 2, $ArCH_2O$), 7.17 (s, 1, aromatic H). Anal. Calcd for $C_{13}H_{13}NO_5$: C, 59.32; H, 4.94; N, 5.32. Found: C, 59.12, H, 4.91; N, 5.16.

SYNTHESIS OF CAMPTOTHECIN ANALOGS

Synthesis of 11-hydroxy-20(RS)-camptothecin and 11-hydroxy-20(S)-camptothecin 11-hydroxy-20(RS)-camptothecin and 11-hydroxy-20(S)-camptothecin are prepared from 11-methoxy-20(RS)- and 11-methoxy-20(S)-camptothecin by demethylation with hydrobromic acid as follows:

11-Methoxy-20(RS)-camptothecin and 11-methoxy-20(S)-camptothecin

A mixture of 4-methoxy-2-aminobenzaldehyde (180 mg, 1.19 mmol) and the tricyclic ketone 13 (300 mg, 1.14 mmol) in toluene (18 mL) was heated under $N_2$ in a flask equipped with a Dean-Stark trap. At reflux p-toluenesulfonic acid (5 mg) was added, and the red-brown solution was heated for an additional 2 hr. The toluene was removed under reduced pressure to give a brown solid which was treated with water (10 mL) and chloroform (20 mL). The aqueous phase was extracted with additional chloroform (3×20 mL) and the combined extracts dried ($Na_2SO_4$). Evaporation gave a brown solid which was recrystallized from methanol-chloroform to give 216 mg (50%) of compound as a tan solid: 275°–279° C.; mass spectrum (electron impact), m/z 378. 1219 $M^+$; $C_{21}H_{18}N_2O_5$ requires 378. 1214;

$v_{max}$ (KBr) 3480 (OH), 1745 (lactone), 1660 (pyridone), 1622, 1236 and 1152 cm$^{-1}$; $^1$H-NMR (DMSO-d$_6$) δ 0.87 (t, 3, J=7 Hz, H-18), 1.85 (m, 2, H-19), 3.95 (s, 3, 11-OCH$_3$), 5.24 (s, 2, H-5), 5.42 (s, 2, H-17), 7.32 (s, 1, H-14), 7.37 (dd, 1, J =9, 2.5 Hz, H-10), 7.56 (d, 1, J =2.5 Hz, H-12), 8.02 (d, 1, J=9 Hz, H-9), 8.60 (s, 1, H-7).

11-Hydroxy-20-RS) - and 11-hydroxy-20(S)camptothecin 11-methoxy-20 (RS) - or 11-methoxy-20 (S) -camptothecin (75 mg) was combined with 48% aqueous HBr (2.5 mL) and heated at reflux for 6 hr. The red-brown mixture was stripped of solvent under high vacuum. Chromatography of the residue through silica gel (15 g) (7% MeOH-CHCl$_3$) gave the 11-hydroxy compound (33 mg, 45%) which was further purified by recrystallization from 13% MeOH in CHCl$_3$: mp 323°-326° C.; mass spectrum (electron impact), m/z 364.1054 M$^+$, C$_{20}$H$_{16}$N$_2$O$_5$ requires 364. 1059; $v_{max}$ (KBr) 3450, 1742, 1654, 1613, 1592, 1570, 1245 cm $^{-1}$; $v_{max}$ (EtOH), 224 (log ε 4.58), 259, (4.39), 353 (4.16), 371 (4.19), 387 (4.20); $^1$H-NMR (DMSO-d$_6$): δ 0.88 (t, 3, J=7 Hz, H-18), 1.85 (m, 2, H-19), 5.20 (s, 2, H-5), 5.41 (s, 2, H-17), 6.51 (br s, 1, OH-20), 7.26 (dd, 1, J=9, 2.5 Hz, H-10), 7.28 (s, 1, H-14).

10-Hydroxy-20(RS)- and 10-hydroxy-20(S)-camptothecin

These compounds are prepared in a manner analogous to that described for the 11-hydroxycamptothecins using 5-methoxy-2-aminobenzaldehyde which is reacted with the tricyclic ketone 11 in the presence of p-toluenesulfonic acid. The product is 10-methoxy-20(RS)- or 10-methoxy-20(S)-camptothecin which on treatment with refluxing hydrobromic acid as described for the 11-hydroxycamptothecins, gives the 10-hydroxy-20(RS)- and 10-hydroxy-20(S) camptothecins.

9-Methoxy-20(RS)- and 9-methoxy-20(S)-camptothecin 9-Hydroxy-20(RS)- and 9-hydroxy-20(S)-camptothecins In a manner analogous to that described for 11-methoxy-20(RS)- and 11-methoxy-20(S)-camptothecin, 6-methoxy-2-aminobenzaldehyde is treated with the tricyclic 11 ketone in the presence-of p-toluenesulfonic acid yielding 9-methoxy-20(RS)- and 9-methoxy-20(S)-camptothecin. Demethylation with hydrobromic acid gives 9-hydroxy-20(RS)- and 9-hydroxy-20(S)-camptothecin.

10-Nitro-20(RS)- and 10-nitro-20(S),camptothecin

A mixture of 2-amino-5-nitrobenzaldehyde (95 mg, 0.57 mmol) and the tricyclic ketone 11 (150 mg, 0.57 mmol) was heated at 120° C. for 10 min. The temperature was raised to 160° C., and the dark molten mass was kept at this temperature for 1.5 hr with occasional stirring. Chromatography of the residue through silica gel (20 g) using 0.5% MeOH in CHCl$_3$ afforded the title compounds (108 mg) as yellow solids; mp 297°-300° C. (decomp.); mass spectrum (electron impact), m/z 393.0965 M$^+$, C$_{20}$H$_{15}$N$_3$O$_6$ requires 393.0960;$v_{max}$ (KBr) 3450 (OH), 1745 (lactone), 1660 (pyridone), 1620, 1350, and 1160 cm$^{-1}$; $^1$H-NMR (TFA-d) δ 1.14 (t, 3, J=7 Hz, H-18), 2.15 (m, 2, H-19), 5.88 (s, 2, H-5), 5.68 (Abq, 2, J=17 Hz, Δγ=85 Hz, H-17), 8.43 (s, 1, H-14), 8.70 (d, 2, J=8 Hz, H-12), 9.05 (d, 2, J=8 Hz, H-11), 9.35 (s, 1, H-9), 9.60 (s, 1, H-7).

10-Amino-20 (RS) - and 10-amino-20 (S) -camptothecin

A suspension of 10-nitro-20 (RS) - or 10-nitro-20 (S)-camptothecin (100 mg) and 10% Pd/C (40 mg) in absolute EtOH (40 mL) was stirred in an atmosphere of H$_2$ at room temperature for 30 min. Filtration through Celite and removal of the solvent under reduced pressure gave tan yellow solids (86 mg crude). Recrystallization from 13% MeOH/CHCl$_3$ gave the pure product (30 mg) as an olive-yellow solid: mp, softening at 135 ° C., gradual blackening upon further heating; mass spectrum (electron impact), m/z 363. 116 M$^+$; C$_{20}$H$_{17}$N$_3$O$_4$ requires 363. 1218; $v_{max}$ (KBr) 3440 (OH, NH 1750 (lactone), 1660 (pyridone) cm$^{-1}$. $^1$H-NMR (TFA-d) δ 1.06 (t, 3, J =7Hz, H-18), 2.08 (d, J =7Hz, H-17), 5.89 (s, 2, H-5), 5.70 (Abq, 2, J =17Hz, Δγ=85Hz, H-17), 8.34 (d, J =9Hz, H-12), 8.64 (d, J =9Hz, H-11), 9.26 (s, 1, H-()), 9.43 (s, 1, H-7) .

9-Nitro-20(RS)- and 9-nitro-20(S)-camptothecin; 9-amino-20(RS)- and 9-amino-20(S)-camptothecin A mixture of 2-amino-6-nitrobenzaldehyde is treated with the tricyclic ketone 11 in the manner described for the 10-nitro series above yielding 9-nitro-20(RS)- and 9-nitro-20(S)-camptothecin. This compound, after reduction with palladium/carbon, yielded 9-amino-20(RS)- and 9-amino-20(S)-camptothecin. Alternatively, the 9-amino compound is obtained in one step by reaction of 2,6-diaminobenzaldehyde with ketone 11.

11-Nitro-20(RS)- and 11-nitro-20(S)-camptothecin; 11-amino-20(RS)- and 11-amino-20(S)-camptothecin In a manner similar to that described for 10-nitro-20(RS)- and 10-nitro-20(S)-camptothecin, a mixture of 2-amino-4-nitrobenzaldehyde is treated with the tricyclic ketone 11 yielding 11-nitro-20(RS)- or 11-nitro-20(S)-camptothecin which in turn is reduced to 11-amino compound camptothecin by palladium/carbon. Alternatively, the 11-amino-20(RS)- or 11-amino-20(S)-camptothecin is obtained by reaction of 2,4-diaminobenzaldehyde with ketone 11.

10,11-Dihydroxy-20(RS)- and 10,11-dihydroxy-20(S)-camptothecin

A solution of the crude dibenzyloxy aminoacetal (400 mg) and the tricyclic ketone 11 (132 mg, 0.5 mmol) in toluene (60 mL) was refluxed for 8 hr. It was filtered hot, and the pure dibenzylether was collected upon cooling (200 mg, 81%); mp 276° C. $v_{max}$ (KBr) 3440, 1740, 1650, 1590, 1490, 1440, 1380, 1250, 1140, 1100 cm$^{-1}$; 250 MHz $^1$H-NMR (DMSO-d$_6$) δ 0.88 (t, 3, J =7 Hz, H-18), 1.86 (m, 2, H-19), 5.22 (s, 2, H-17), 5.34 (s, 2,10-OCH$_2$-C$_6$H$_5$), 5.39 (s, 2, 11-OCH$_2$-C$_6$H$_5$), 5.41 (s, 2, H-5), 6.5 (s, 1, OH), 7.25 (s, 1, H-14) 7.35-7.65 (m, 12, H-9, 12, —OCH$_2$—C$_6$H$_5$), 8.44 (s, 1, H-7). Anal. calcd for C$_{34}$H$_{28}$N$_2$O$_6$: C, 72.84; H, 5.03; N, 5.00. Found C, 72.91; H, 5.09; N, 4.96.

The dibenzyl ether (130 mg, 0.23 mmol) was mildly refluxed for 2 hr in 24% HBr (50 mL). The acid was removed, and the residue was dissolved in hot methanol (50 mL). Ether (50 mL) was added at room temperature and the yellow powdery dihydroxy camptothecin hydrobromide was collected (122 mg, 77%) mp>300° C. $v_{max}$ (KBr) 3400 (b), 1740, 1655, 1585, 1545, 1510, 1395, 1300, 1270, 1200, 1160 cm$^{-1}$; $^1$H NMR (DMSO, d$_6$): δ 0.88 (t, 3, J=7 Hz, H-18), 1.85 (m, 2, H-19), 5.20 (s, 2, H-17), 5.42 (s, 2, H-5), 7.31 (s, 2, H-9, H-14), 7.40 (s, 1, H-12 ), 8.45 ( s, 1, H-7). Anal. calcd for $C_{20}H_{17}BrN_2O_6.0.5\ H_2O$: C, 51.08; H, 3.86; N, 5.95; 3r, 16.99. Found C, 51.09; H, 4.04; N, 5.78; 3r, 16.83.

Dihydroxy hydrobromide salt (110 mg, 0.23 mmol) was suspended in water (10 mL). Sodium hydroxide (0.1 N, 7.2 mL) was added and the mixture was agitated. The resulting clear solution was acidified using 5N HCl; and after an hour, the sample was centrifuged, the supernatant liquid was decanted and the process repeated with additional water (20 mL). The residue was dried (78 rag, 74%); mp>300° C. $\nu_{max}$ (KBr): 3490, 3000 (b), 1740, 1645, 1590, 1460, 1385, 1265, 1190, 1150 cm$^{-1}$. $^1$H NMR (DMSO, d$_6$): δ 0.88 (t, 3, J=7 Hz, H-18), 1.87 (q, 2, H-19), 5.20 (s, 2, H-17), 5.42 (S, 2, H-5), 7.35 (s, 1, H-14), 7.44 (s, 1, H-9), 7.52 (s, 1, H-12), 8.51 (s, 1, H-7). Anal. calcd for $C_{20}H_{16}N_2O_6.0.75\ H_2O$: C, 61.06; H, 4.44; N, 7.12. Found C, 61.12; H, 4.44; N, 7.09.

10-Chloro-20(RS)- and 10-chloro-20(S)-camptothecin

These compounds were prepared by treating 5-chloro-2-aminobenzaldehyde with the tricyclic ketone 11.

A solution of the 5-chloro-2-aminobenzaldehyde (80 mg, 0.51 mmol) and the tricyclic ketone 11 (100 mg, 0.38 mmol) in toluene (60 mL) was refluxed for 15 min. p-Toluenesulfonic acid (10 mg) was then added, and refluxing was continued for an additional 5 hr. The solvent was removed in vacuo and the residue chromatographed (silica gel 60, 2% MeOH-CHCl$_3$). The product obtained was recrystallized from CHCl$_3$-MeOH-EtOAc; mp 270° C., 60 mg (41%). $\nu_{max}$ (KBr), 3430, 1745, 1655, 1600, 1495, 1230, 1160 cm$^{-1}$. 250 MHz $^1$H-NMR (TFA-d$_1$) δ 1.15 (t, 3, J=7 Hz, H-18), 2.16 (m, 2, H-19), 5.73 (ABq, 2, J=17 Hz, Δγ=85 Hz, H-17), 5.84 (s, 2, H-5), 8.29 (d, 1, J=9 Hz, H-11), 8.35 (s, 1, H-14), 8.40 (s, 1, H-9), 8.45 (d, 1, J=9 Hz, H-12), 9.31 (s, 1, H-7). Anal. calcd for $C_{20}H_{15}C_1N_2O_4.0.5\ H_2O$: C, 61.47; H, 4.12; N, 7.17; Cl, 9.07. Found C, 61.41; H, 4.12; N, 7.12; Cl, 9.11.

10-Methyl-20(RS)- and 10-methyl-20(S)-camptothecin

5-Methyl-2-aminobenzaldehyde was treated with the tricyclic ketone 11 to give the title compounds.

The tricyclic ketone 11 (130 mg, 0.5 mmol) and the 5-methyl-2-aminobenzaldehyde (560 mg) in toluene (60 mL) were refluxed for 0.5 hr. Acetic acid (1 mL) and p-toluenesulfonic acid (35 mg) were added, and refluxing was continued for an additional 5 hr. The solvent was removed in vacuo, and the residue was triturated with warm ether (30 mL). The product was recrystallized from chloroform-methanol-ether to yield pure compound (102 mg, 57%), mp 278°–280° C. $\lambda^{max}$ (KBr) 3460, 2980, 1740, 1655, 1590, 1550, 1470, 1450, 1370, 1260, 1240, 1160, 1050 cm$^{-1}$. 250 MHz $^1$H-NMR (DMSO-d$_6$) δ 0.89 (t, 3, J=7 Hz, H-18), 1.87 (q, 2, H-19), 2.54 (s, 3, 10-CH$_3$), 5.24 (s, 2, H-17), 5.42 (s, 1, H-5), 7.31 (s, 1, H-14), 7.69 (d, 1, J=8.6 Hz, H-11), 7.86 (s, 1, H-9), 8.05 (d, 1, J=8.6 Hz; H-12), 8.55 (s, 1, H-7). Anal. calcd for $C_{21}H_{18}N_2O_4.0.25\ H_2O$: C, 68.75; H, 5.08; N, 7.64. Found C, 68.74; H, 5.08; N, 7.64.

11-Formyl-20(RS)- and 11-formyl-20(S)camptothecin

2-Nitroterephthaldicarboxaldehyde was converted to the ethylene diacetal by conventional methods and reduced using Na$_2$S. A solution of the nitro diacetal (4.1 g, 17.5 mmol), Na$_2$S (14 g) in 80% ethanol (15 mL) was refluxed for 1 hr. Ethanol was removed in vacuo, the reaction mixture was diluted with water (10 mL) and the aqueous phase was extracted with CH$_2$Cl$_2$ (4×50 mL). The organic phase was washed with water, dried (MgSO$_4$), and evaporated to give the aminodiacetal, which was recrystallized from ethyl acetate-hexane (2.8 g, 78%); mp 76° C. $\nu_{max}$ (KBr) 3480, 3395, 3000, 2960, 2900, 1625, 1445, 1395, 1085, 950 cm$^{-1}$. 60 MHz $^1$H NMR (CDCl$_3$-D$_2$O) δ 4.0 (m, 8, —OCH$_2$CH$_2$O—), 5.6 (s, 1, —O—CH$_2$—O—, C-4), 5.7 (s, 1, —O—CH$_2$—O—, C-1), 6.6 (s, 1, H-3), 6.65 (d, 1, J=8 Hz, C-5), 7.2 (d, 1, J=8 Hz, H-6). Anal. calcd for $C_{12}H_{15}NO_4$: C, 60.66; H, 6.36; N, 5.90. Found C, 60.79; H, 6.41; N, 5.84.

A solution of the tricyclic ketone 11 (265 mg, 1.0 mmol), aminodiacetal (500 mg, 2.1 mmol, 300 mg initially, 100 mg each at intervals of 5 and 10 hr) in toluene (70 mL) was refluxed for 0.5 hr. Acetic acid (2 mL) was added and refluxing continued for 18 hr. The solvent was evaporated in vacuo, and the residue was taken up in 75% methanol (250 mL). Conc. HCl 3 mL) was added and the reaction mixture heated at 50°–60° C. for 24 hr. The mixture was filtered, and the residue was washed with water and recrystallized from CHCl$_3$-MeOH-EtOAc. mp: 276°–279° C. (175 mg, 45%). $\nu_{max}$ (KBr) 3460, 1745, 1690, 1655, 1600, 1200, 1150, 1135 cm$^{-1}$. 250 MHz $^1$H NMR (TFA-d$_1$), δ 1.16 (t, 3, J=7 Hz, H-18) 2.16 (g, 2, J=7 Hz, H-19), 5.78 (ABq, 2, J=18 Hz, Δγ=85 Hz, H-17), 5.89 (s, 2, H-5), 8.43 (s, 1, H-14), 8.66 (d, 1, J=8.5 Hz, H-10), 8.60 (d, 1, J=8.5 Hz, H-9), 9.12 (s, 1, H-12), 9.49 (s, 1, H-7), 10.42 (s, 1, CHO)-Anal. calcd. for $C_{21}H_{16}N_2O_5.H_2O$: C, 64.01; H, 4.56; N, 7.11. Found C, 64.08, H, 4.21; N, 6.84.

11-Cyano-20(RS)- and 11-Cyano-20(S)-camptothecin

A mixture of 11-formyl-20(RS)- or 11-formyl-20(S)-camptothecin (225 mg, 0.6 mmol), hydroxylamine hydrochloride (50 mg, 0.72 mmol), sodium formate (90 mg, 1.3 mmol), and formic acid (6 mL) was refluxed for 1.5 hr. The mixture was evaporated to dryness in vacuo, and the residue was washed with water, dried and chromatographed (silica gel 60, 0.5% MeOH-CHCl$_3$) and recrystallized from CHCl$_3$-EtOAc to yield the 11-cyano compound (65 mg, 29%): mp 288° C. $\nu_{max}$ (KBr) 3400, 2235, 1735, 1655, 1590, 1450, 1400, 1230, 1150, 1110, 1045 cm$^{-1}$. 250 MHz $^1$H NMR (DMSO-d$_6$): δ 0.88 (t, 3, J=7 Hz, H-18), 1.88 (m, 2, H-19), 5.32 (s, 2, H-17), 5.44 (s, 2, H-5), 7.35 (s, 1, H-14), 7.98 (d, 1, J=8.5 Hz, H-10), 8.32 (d, 1, J=8.5 Hz, H-9), 8.74 (s, 1, H-12), 8.80 (s, 1, H-7). Anal. calcd for $C_{21}H_{15}N_3O_4.1.5\ H_2O$: C, 62.99; H, 4.52; N, 10.49. Found C, 62.99; H, 3.95; N, 10.20.

Alternatively, the 11-cyano compounds can be prepared by the reaction of 5-cyano-2-aminobenzaldehyde with the tricyclic ketone 11.

PREPARATION OF CAMPTOTHECIN ANALOGS WITH MODIFIED A RING STRUCTURE

The reaction of the tricylic ketone 11 with suitable precursors other than substituted ortho-aminobenzaldehydes can be used to give active new camptothecin analogs exemplified by the following nonlimiting examples:

10-Aza-20 (RS) - and 10-aza-20 (S) -camptothecin

A solution of 4-aminonicotinaldehyde (24.2 mg, 0.198 mmol), the tricyclic ketone 11 (53.5 mg, 0.203 mmol) and p-TsOH . H$_2$O (2 mg) in toluene (25 mL) was refluxed for 4 days using Dean-Stark trap. The solvent was removed under reduced pressure, and the residue was chromatographed through silica gel (20 g) using CHCl$_3$-acetone-MeOH (5:1:1). The product was crystallized from 13% MEOH in CHCl$_3$ and EtOAc: mp 289°–292° C.; mass spectrum (electron impact), m/z 349.1061 M+; C$_{19}$H$_{15}$N$_3$O$_4$ requires 349. 1066; $\nu_{max}$ (KBr) 3320 (OH), 1730 (lactone), 1650 (pyridone), 1600 (aromatic) cm$^{-1}$; $^1$H NMR (CDCl$_3$) δ 1.05 (t, 3, J=7.3 Hz, H-18), 1.92 (m,2, H-19), 5.35 (s, 2, H-5), 5.52 (ABq, 2, J=18 Hz, Δγ=85 Hz, H-17), 7.74 (s, 1, H-14), 8.04 (d, 1, J=5.5 Hz, H-12), 8.53 (s, 1, H-7), 8.84 (d, J=5.5 Hz, H-11), 9.4 (s, 1, H-9).

A-Nor-9-thia-20(RS)- and
A-nor-9-thia-20(S)-camptothecin

These sulfur containing camptothecin analogs are prepared by the reaction of 3-amino-2-formylthiophene with tricyclic ketone 11.

A solution of 3-amino-2-formylthiophene (79 mg, 0.62 mmol) and the tricyclic ketone 11 (96 mg, 0.37 mmol) in toluene (1.5 mL) was brought to reflux and then cooled before adding a crystal of p-toluenesulfonic acid. The mixture was refluxed for 2.5 hr under N$_2$, cooled and the precipitate filtered. The crude material was chromatographed on silica gel (20 g) by elution with 2% MeOH in CHCl$_3$. Crystallization of the product from 13% MeOH-CHCl$_3$ and EtOAc yielded the title compounds as yellow solids (19 mg, 15%): mp 297°–298° C.; $\nu_{max}$ 1740 (lactone), 1655 cm$^{-1}$ (pyridone); $^1$H NMR (TFA-d$_1$) δ 1.05 (t, 3, J=7 Hz, H-18), 2.07 (q, 2, J=7 Hz, H-19), 5.60 (m, 2, H-17), 5.65 (s, 2, H-5), 7.89 (d, J=6 Hz, H-11), 8.05 (s, 1, H-14), 8.57 (d, J=6 Hz, H-10), 9.23 (s, 1, H-7). Anal. (C$_{18}$H$_{14}$N$_2$O$_4$S), calcd. C, 61.02; H, 3.95; N, 7.91. Found C, 60.65; H, 4.01; N, 7.78.

10,11-Methylenedioxy-20 (RS)- and
10,11-methylenedioxy-20 (S)-camptothecin

The required ortho-aminoaldehyde was prepared by reduction of 2-nitropiperonal. This compound (60 mg, 0.36 mmol) and the tricyclic ketone 11 (53 mg, 0.20 mmol) were refluxed for 8 hr in toluene (30 mL) containing p-TsOH . H$_2$O (8 mg). The solvent was removed in vacuo, the red residue adsorbed onto Celite (1 g) and chromatographed through silica gel (10 g) using 3% MeOH in CHCl$_3$, Concentration of the appropriate fractions gave the 10,11-methylenedioxy compound (36 mg, 45%) as a pale tan solid. Crystallization of this material from CHCl$_3$ gave the analytical sample as a cream-colored solid: mp >250° C. (decomp); $\nu_{max}$ (KBr) 1750 (lactone), 1655 (pyridone), 1585 cm$^{-1}$ (aromatic); $^1$H NMR (TFA-d$_1$) δ 1.15 (t, 3, J=7 Hz, H-18), 2.16 (q, 2, J=7 Hz, H-19), 5.76 (ABq, 2, J=17 Hz, Δγ=85 Hz, H-17), 5.73 (s, 2, H-5), 6.44 (s, 2, OCH$_2$O), 7.55 (s, 1, H-14), 7.69 (s, 1, H-9), 8.16 (s, 1, H-12), 9.05 (s, 1, H-7). Anal. calcd for C$_{21}$H$_{16}$N$_2$O$_6$: 392. 1008. Found 392. 1009 (C$_{21}$H$_{16}$N$_2$O$_6$.1.0 H$_2$O).

10,11-Methylenedioxy-20(RS)- and
10,11-methylenedioxy-20(S)-camptothecin Sodium Salt The title compounds were prepared from 10,11-methylenedioxy-20(RS)-camptothecin (Wani et al., *J. Med. Chem,* 29, 2358 (1986)) by hydrolytic action of sodium hydroxide. Thus, 10,11-methylenedioxy-20(RS)- or 10,11-methylenedioxy-20(S)-camptothecin (77 mg, 0.194 mmol) was suspended in 90% aqueous methanol (30 mL) and treated with 0.1 N aqueous sodium hydroxide (1.94 mL, 0.194 mmol). Upon heating at 50°–60° C. for 1 hr under nitrogen a clear solution resulted which was cooled to ambient temperature and evaporated to dryness. The residue was dissolved in distilled water (2 mL) and filtered (0.45 micron membrane), and the resulting solution evaporated. The residue was recrystallized from ethanol/ether to provide a pale yellow solid (53 mg, 65%), mp >300° C.; IR $\nu_{max}$ (KBr) 3400 (br), 2970, 2920, 1640, 1610, 1560–1580, 1497, 1466, 1370, 1246, 1225, 1183, 1030, 1000, 947, 855, 810, 761, 708 and 560–580; $^1$H NMR (DMSO-d$_6$) δ 0.85 (t, 3, J =7 Hz, H-18), 2.09 (m, 2, H-19), 4.74 (ABq, 2, Δγ=68 Hz, J =12, 4 Hz, H-17), 5.12 (s, 2, H-5), 5.64 (dd, 1, J 4, 7 Hz, 17-OH), 6.17 (s, 1, 20-OH), 7.47 (s, 1, H-14), 7.54 (s, 1, H-9), 7.62 (s, 1, H-12, 8.41 (s, 1, H-7).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of inhibiting the enzyme topoisomerase I in a mammal, comprising:
administering to said mammal an effective inhibitory amount of 9-amino-20(S)-camptothecin free of 9-amino-20(R)-camptothecin, 10-amino-20(S)-camptothecin free of 10-amino-20(R)-camptothecin or 10,11-methylenedioxy-20(S)-camptothecin sodium salt free of 10,11-methylenedioxy-20(R)-camptothecin sodium salt.

2. A method of inhibiting the enzyme topoisomerase I in a mammal, comprising administering to said mammal an effective inhibitory amount of 9-amino-20(S)-camptothecin free of 9-amino-20(R)-camptothecin.

3. A method of inhibiting the enzyme topoisomerase I in a mammal, comprising administering to said mammal an effective inhibitory amount of 10-amino-20(S)-camptothecin free of 10-amino-20(R)-camptothecin.

4. The method of claim 1, comprising administering 10,11-methylenedioxy-20(S)-camptothecin sodium salt free of 10,11-methylenedioxy-20(R)-camptothecin sodium salt.

* * * * *